United States Patent
Carlucci et al.

(10) Patent No.: US 6,570,059 B1
(45) Date of Patent: May 27, 2003

(54) ABSORBENT ARTICLE WITH BREATHABLE BACKSHEET COMPRISING ONE LAYER WITH IMPROVED CAPILLARY APERTURES

(75) Inventors: Giovanni Carlucci, Chieti (IT); Paolo Veglio, Pescara (IT); Amedeo Franco D'Incecco, Pescara (IT); Luigi Marinelli, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/914,859

(22) PCT Filed: Mar. 31, 2000

(86) PCT No.: PCT/US00/08809
§ 371 (c)(1),
(2), (4) Date: Sep. 4, 2001

(87) PCT Pub. No.: WO00/59433
PCT Pub. Date: Oct. 12, 2000

(30) Foreign Application Priority Data

Apr. 1, 1999 (EP) .............................................. 99105192

(51) Int. Cl.⁷ ................................................. A61F 13/15
(52) U.S. Cl. ...................................... 604/383; 604/367
(58) Field of Search ........................... 604/383, 385.01, 604/367, 378

(56) References Cited

U.S. PATENT DOCUMENTS

| 3,881,489 A | 5/1975 | Hartwell |
| 3,989,867 A | 11/1976 | Sisson |
| 4,306,559 A * | 12/1981 | Nishizawa et al. ......... 604/371 |
| 4,681,793 A * | 7/1987 | Linman et al. ............. 428/138 |
| 5,591,510 A | 1/1997 | Junker et al. |
| 6,232,521 B1 * | 5/2001 | Bewick-Sonntag et al. . 604/378 |
| 6,413,247 B1 * | 7/2002 | Carlucci et al. ....... 604/385.01 |
| 6,436,080 B1 * | 8/2002 | Carlucci et al. ....... 604/385.01 |

FOREIGN PATENT DOCUMENTS

| EP | 0 203 823 A2 | 12/1986 |
| EP | 0 813 849 A1 | 12/1997 |
| EP | 0 934 736 A1 | 8/1999 |
| GB | 2 295 322 A | 5/1996 |

* cited by examiner

Primary Examiner—Weilun Lo
Assistant Examiner—Jamisue A Webb
(74) Attorney, Agent, or Firm—Kevin C. Johnson

(57) ABSTRACT

The present invention relates to breathable absorbent articles like baby diapers, adult incontinence articles and in particular to sanitary napkins or pantiliners. According to the present invention the articles are provided with an apertured backsheet for breathability. At least one of the breathable layers of the backsheet comprises a resilient, three dimensional web which consists of a liquid impervious polymeric film having apertures. The apertures form capillaries which are designed such that the backsheet provides an increased barrier to liquid passage out of the article and maintains water vapor permeability when the web is exposed to compressive pressure.

7 Claims, 3 Drawing Sheets

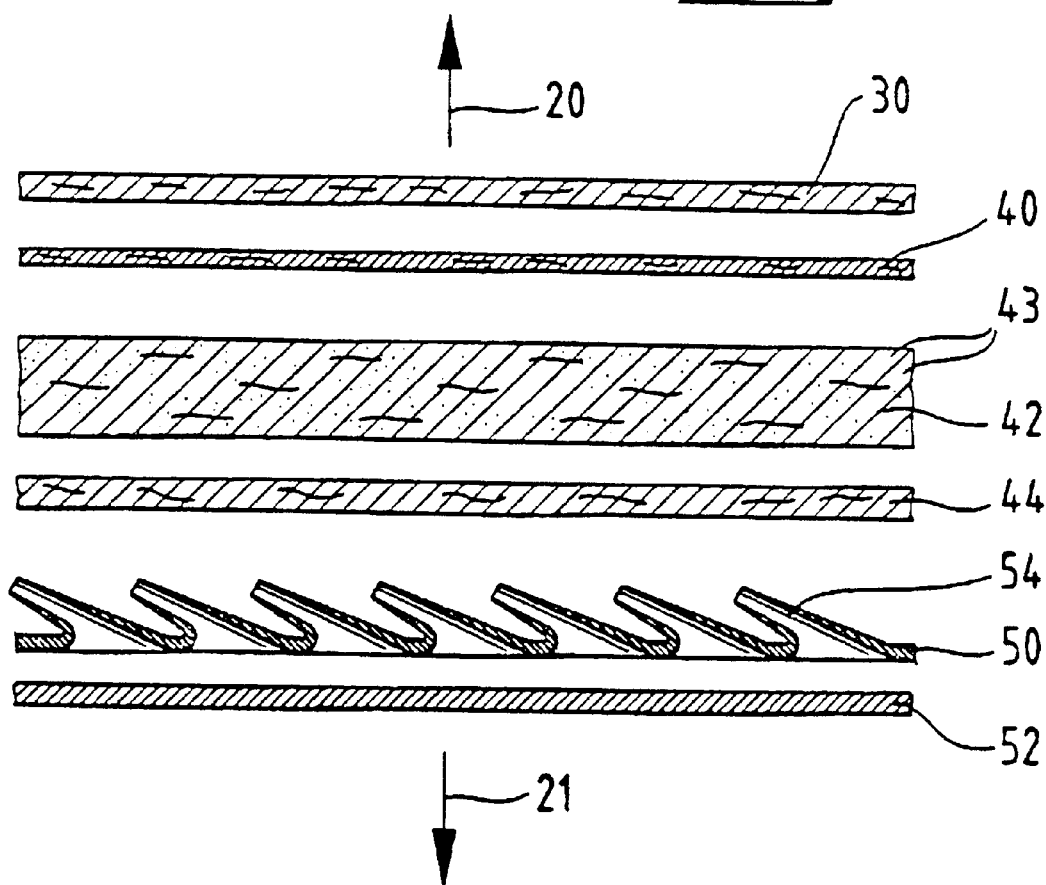
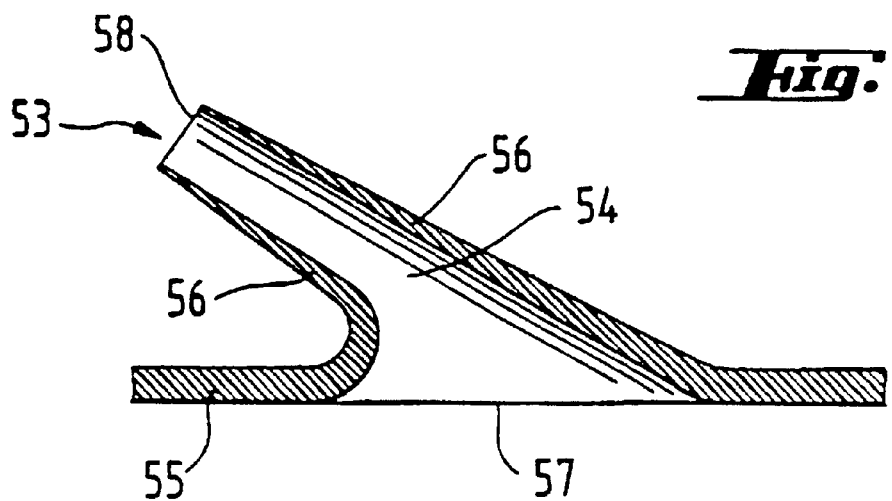

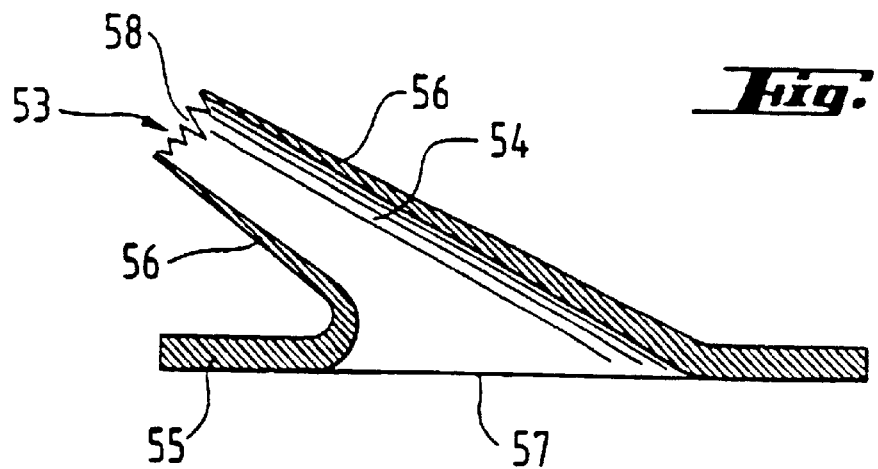
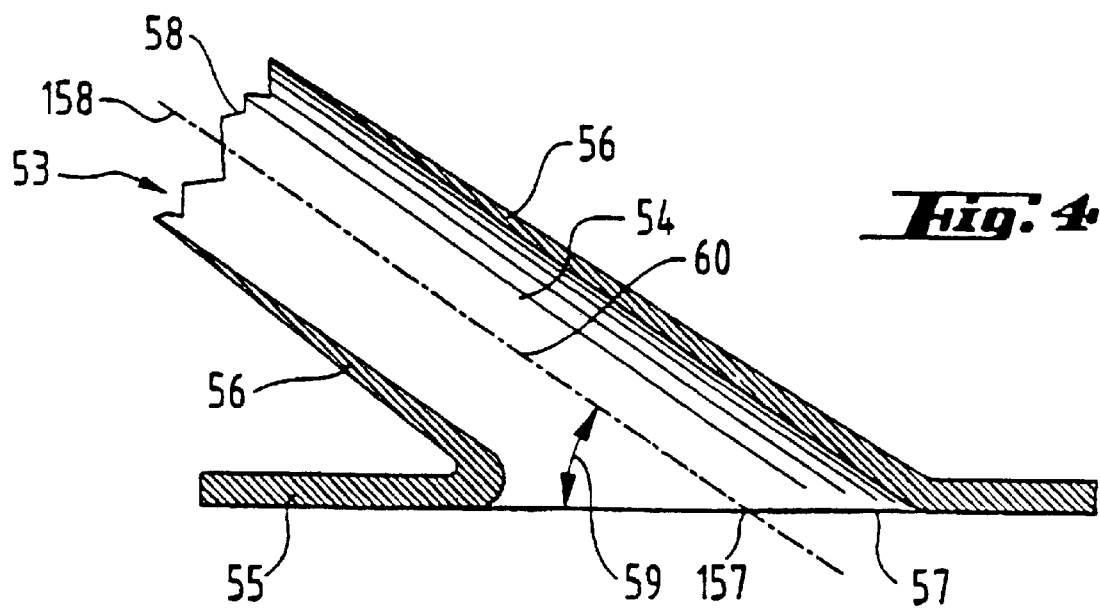

ABSORBENT ARTICLE WITH BREATHABLE BACKSHEET COMPRISING ONE LAYER WITH IMPROVED CAPILLARY APERTURES

FIELD OF THE INVENTION

The present invention relates to breathable absorbent articles like baby diapers, adult incontinence articles and in particular to sanitary napkins or pantiliners. According to the present invention the articles are provided with an apertured backsheet for breathability. At least one of the breathable layers of the backsheet comprises a resilient, three dimensional web which consists of a liquid impervious polymeric film having apertures. The apertures form capillaries which are designed such that the backsheet provides an increased barrier to liquid passage out of the article and maintains water vapour permeability when the web is exposed to compressive pressure.

BACKGROUND OF THE INVENTION

The primary consumer needs which underlie development in the absorbent article field, in particular sanitary napkins, catamenials, or pantiliners is the provision of products providing both a high protection and comfort level.

One means for providing consumer comfort benefits in absorbent articles is by the provision of breathable products. Breathability has typically concentrated on the incorporation of so called 'breathable backsheets' in the absorbent articles. Commonly utilised breathable backsheets are microporous films and apertured formed films having directional fluid transfer as disclosed in for example U.S. Pat. No. 4,591,523. Both these types of breathable backsheets are vapour permeable allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use, commonly associated with the presence of an apertured formed film or film like topsheet.

A drawback associated with the use of breathable backsheets in absorbent articles is the negative effect on the protection level performance by leakage, known as wet through, onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the backsheet is compressed e.g. during physical exertion, especially for heavy discharge loads or over extended periods of time. Thus, whilst the incorporation of breathable backsheets in absorbent articles is highly desirable from a comfort standpoint, since the primary role of a backsheet still remains the prevention of liquid leakage, conventional breathable backsheets have not always been satisfactorily incorporated into products.

The problem of wet through onto users garments due to the incorporation of such breathable backsheets in absorbent articles has indeed also been recognized in the art. Attempts to solve the problem have mainly resided in the use of multiple layer backsheets such as those illustrated in U.S. Pat. No. 431,216. Similarly European patent application no. 710 471 discloses a breathable backsheet comprising an outer layer of a gas permeable, hydrophobic, polymeric fibrous fabric and an inner layer comprising an apertured formed film having directional fluid transport. The backsheet construction preferably has no liquid transport/wet through under certain specified test conditions. Also European patent application no. 710 472 discloses a breathable backsheet consisting of at least two breathable layers which are unattached to one another over the core area. The backsheet construction preferably has no liquid transport/wet through under certain specified test conditions.

U.S. Pat. No. 4,713,068 discloses a breathable clothlike barrier for use as an outer cover for absorbent articles. The barrier comprises at least 2 layers, a first layer having a specified basis weight, fiber diameter and pore size and a second layer comprising a continuous film of poly(vinyl alcohol) having a specified thickness. The barrier also has a specified water vapour transmission rate and level of impermeability.

However, none of the above proposed solutions have been able to provide a fully satisfactory solution to the problem of wet through prevention under all conditions, especially when the article incl. the breathable backsheet is compressed.

U.S. Pat. No. 5,591,510 as well as WO 97/03118 and WO 97/03795 disclose an apertured film layer having capillaries which are disposed at an angle relative to the plane of the film, which films are referred to as slanted capillary films. This film structure is provided as a improvement for incorporation into clothing and garments which are breathable, yet non transmitting liquids toward the wearer of such garments. Also the use of such slanted capillary films is indicated in the context of absorbent articles but as a topsheet, particularly in FIG. 16 of U.S. Pat. No. 5,591,510 the combination of such slanted capillary films together with an absorbent material is disclosed, however not in the context of disposable absorbent articles according to the present invention.

Another problem which occurs when the article is put to use and exposed to compressive pressure or high discharge loadings is that the effective breathability is drastically reduced. For example when liquid has contacted a microporous film the water vapour transmission is effectively eliminated. When considering apertured capillary films of the prior art the water vapour transport is also drastically reduced when they are exposed to pressure but remains at a low level.

It is hence an objective of the present invention to provide absorbent articles which have a breathable backsheet designed such that they provide an increased barrier to liquid passage when exposed to pressure while at the same time the water vapour permeability, i.e. what is conventionally understood as breathability, is less reduced than the water vapour permeability of conventional apertured capillary films (provided they are not made from a water vapour permeable material).

It is another objective of the present invention to provide a disposable absorbent article having and maintaining improved breathability while having and maintaining an acceptable level of protection, i.e. being exceptionally leakage resistant, in particular when the article is exposed to pressure.

SUMMARY OF THE INVENTION

The present invention relates to breathable disposable absorbent articles of a layered construction such as baby diapers, adult incontinence articles and in particular sanitary napkins or panty liners. Also articles such as underarm sweat pads, breast pads, or shirt scholars may benefit from the present invention. Typically such articles are of layered construction with each layer or group of layers having a garment facing surface which is oriented to face in the direction of a garment during use of the article and a wearer facing surface facing in the opposite direction. Typically such articles comprise a liquid pervious topsheet forming the wearer facing surface of the article, an absorbent core and a breathable backsheet forming the garment facing surface of the article. The absorbent core is interposed between the topsheet and the backsheet. However, according to the present invention the absorbent core may provide the wearer facing surface of the article such that this surface of the core also provides the functions of the topsheet.

The breathable backsheet is located on the garment facing surface of the absorbent core and comprises at least a first backsheet layer. It can further comprise additional layers such as a second backsheet layer. The first backsheet layer is positioned between the garment facing surface of the absorbent core. In order to provide the article with breathability all backsheet layers are at least water vapor permeable, preferably air permeable. The first backsheet layer comprises a resilient three dimensional web, which consists of a liquid impervious polymeric film which film has apertures. The apertures form capillaries which have side walls which extend away from the wearer facing surface of the film providing the web with three dimensionality. The capillaries have a first opening in the garment facing surface of the film and a second opening at the end of the capillaries spaced apart from the wearer facing surface of the film. Preferably the capillaries extend away from the wearer facing surface of the film at an angle which is less than 90° in respect to the plane of the film.

In co-pending patent applications based on priority document EP 98101867 and EP 98101868 a combination between a slanted capillary film backsheet, an optional second of the film. The center axis is defined as the line which connects the center point of the first opening of a capillary and the center point of the second opening of a capillary.

For some embodiments it is also possible that the first opening of at least some of the capillaries is larger than the second opening of the respective capillary such that the capillaries themselves form cones which have an increase in capillary action in a direction towards the absorbent core. In yet another embodiment according to the present invention the capillaries are curved towards or appear bent towards the plane of the film. In an alternative or in addition thereto the capillaries have a first and a second portion which are different in direction, form, shape, size or combinations thereof.

BRIEF DESCRIPTION OF THE DRAWINGS

FIG. 1 shows a cross-sectional view of an absorbent article comprising all usual elements of such articles including a preferred embodiment of the breathable backsheet with a second layer according to the present invention.

FIGS. 2–4 show particular preferred embodiments of the slanted capillaries used for the three dimensional web of in the breathable backsheet according to the present invention.

DETAILED DESCRIPTION OF THE INVENTION

Figure 5:
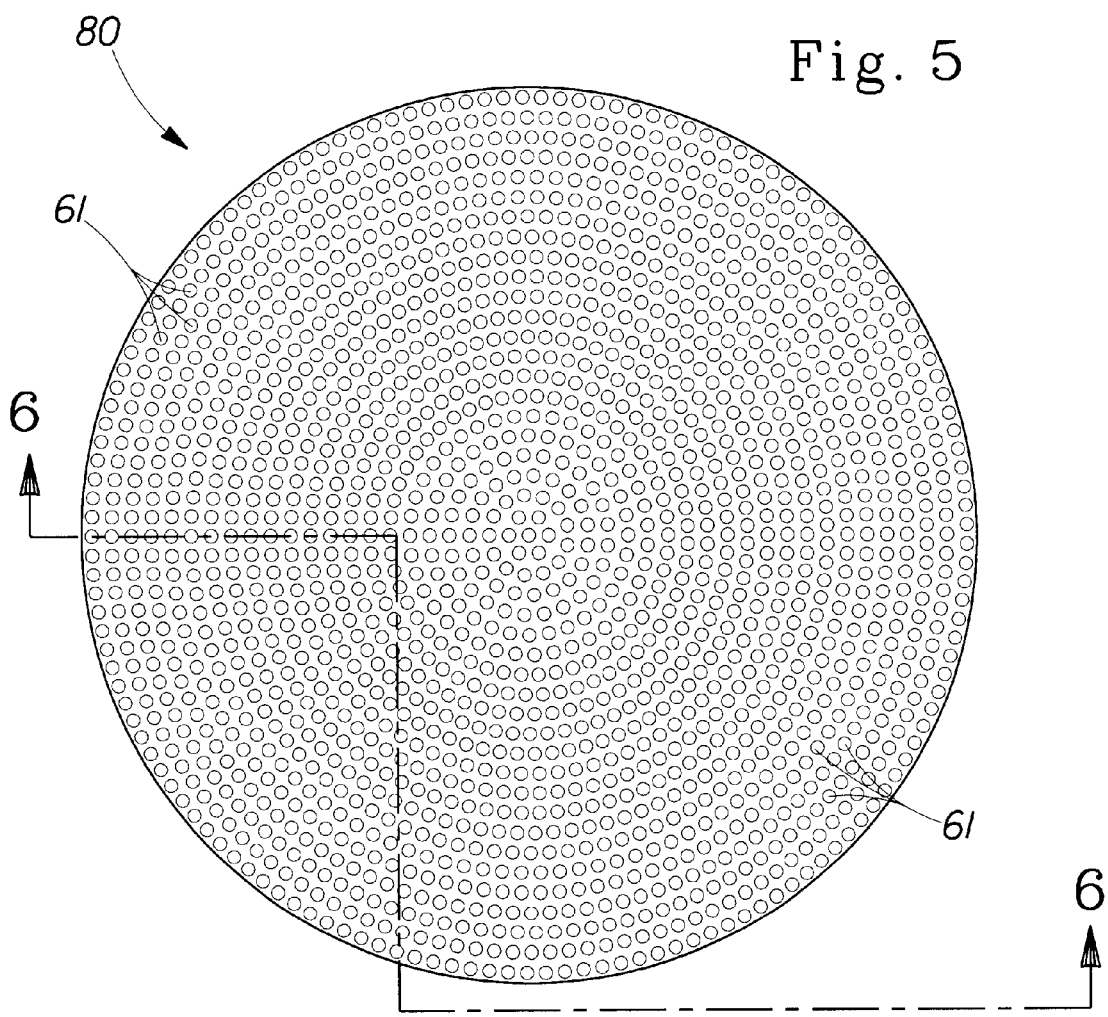
FIGS. 5 and 6 are a top plan view and cross section of the compression plates used in the modified water transmission resistance test.

The present invention relates to absorbent disposable articles such as sanitary napkins, panty liners, incontinence products, sweatpads, breast pads, and baby diapers. Typically such products comprise the elements of a liquid pervious topsheet, a backsheet and an absorbent core intermediate said topsheet and said backsheet. According to the present invention the topsheet, backsheet and core may be selected from any of the known types of these components provided that they meet the desired comfort and protection performance requirements and conditions noted below and in the appended claims.

In general, the topsheet—if present—should have good liquid retention to maintain a dry surface and thereby keep the skin of the wearer dry; the absorbent core needs to layer in the backsheet and a film topsheet have been disclosed. The backsheet construction in these disclosures does provide a major step beyond the here to forth known three dimensional formed film aperture designs or breathable backsheets. However it has now been found that a further step in improving the leakage resistance of absorbent articles and maintenance of their airpermeability can be achieved by the designs according to the present invention. The three dimensional web of the first backsheet layer has a liquid water transport resistance (WTR) in a direction from the second opening towards the first opening of the capillaries in the web towards the outside which is measured by a modified DIN53886 test for WTR. The web also has a water vapour permeability (WVP) in the same direction as the WTR and which can be measured by a modified ASTM E 96-80 test of WVT.

According to the present invention it has surprisingly been found that the WTR, i.e. the liquid water transport resistance increases for the films according to the present invention by at least 50%, preferably by at least 65%, most preferably by at least 75% or more, when comparing the rate at ambient pressure (i.e. no compression) versus a compression of 6865 Pa above ambient. Under the same pressure differential the water vapour permeation, despite an increased water transport resistance is not completely eliminated but reduces by less than 80%, preferably by less than 60% of the WVP at ambient pressure (i.e. without compression).

It is in itself surprising that the webs according to the present invention have an increased resistance to liquid permeation through them when exposing the web to an increased pressure but combining this with the ability to maintain water vapour transport and preferably airpermeability is a considerable surprise to those skilled in the art.

According to the present invention the capillaries are preferably identical and homogeneously distributed across the film at a spacing which does insure the above mentioned limited WVP reduction by less than 80% and preferably by even less than 60% (again when comparing between ambient and the compression under a pressure of 6865 Pa).

Preferably a center axis of each capillary forms an angle between 85° and 20°, more preferably between 65° and 25° and most preferably between 55° and 30° with the plane provide enough absorbent capacity and allow the flow of vapour and/or air through it and the backsheet should prevent wet through (liquid permeability) to retain the absorbed fluid while being sufficiently breathable. Furthermore, the individual elements are joined, preferably using techniques such that the final product has the desired comfort and performance level.

In the following description of the invention the surface facing in the direction of the wearer is called wearer facing surface. In the drawings this direction is indicated by arrow 20. Further the surface facing in the direction of the garment is called garment facing surface and in the drawings this direction is indicated by arrow 21.

Absorbent Article Components

The Topsheet

According to the present invention the absorbent article usually comprises a topsheet. The topsheets suitable for use herein may be any topsheet known in the art. In FIG. 1 the topsheet is indicated with reference numeral 30.

The topsheets for use herein may comprise a single layer or a multiplicity of layers. In a preferred embodiment the topsheet comprises a first layer which provides the user facing surface of the topsheet and a second layer between the first layer and the absorbent structure/core. In addition another layer on the wearer facing surface of the first layer but only extending in the central zone or in parts of the peripheral zone of the article can be desirable to provide extra softness or extra liquid handling/retaining abilities (this design is usually referred to as "hybrid topsheet"). The topsheet typically extends across the whole of the absorbent structure and can extend into and form part of or all of the preferred sideflaps, side wrapping elements or wings.

The topsheet as a whole and hence each layer individually needs to be compliant, soft feeling, and non-irritating to the wearer's skin. It also can have elastic characteristics allowing it to be stretched in one or two directions. As used herein the topsheet hence refers to any layer or combination of layers whose principle function is the acquisition and transport of fluid from the wearer towards the absorbent core and containment of the absorbent core. In addition the topsheet of the present invention should have a high vapour permeability preferably also a high air permeability.

According to the present invention the topsheet may be formed from any of the materials available for this purpose and known in the art, such as wovens, non wovens, films or combinations thereof. In a preferred embodiment of the present invention at least one of the layers of the topsheet comprises a liquid permeable apertured polymeric film. Preferably, the wearer facing and contacting layer is provided by a film material having apertures which are provided to facilitate liquid transport from the wearer facing surface towards the absorbent structure, as detailed for example in U.S. Pat. Nos. 3,929,135, 4,151,240, 4,319,868, 4,324,426, 4,343,314 and 4,591,523. However, even non-woven or woven substrates can be apertured to improve their function of liquid acquisition.

Absorbent Core

According to the present invention the absorbent cores suitable for use herein may be selected from any of the absorbent cores or core system known in the art. As used herein the term absorbent core refers to any material or multiple material layers whose primary function is to absorb, store and distribute fluid. In FIG. 1 the absorbent structure is shown to comprise 3 layers 40, 42, and 44.

The absorbent core of the present invention should have a high vapour permeability preferably also a high air permeability. The absorbent core preferably has a caliper or thickness of less than 12 mm, preferably less than 8 mm, more preferably less than 5 mm, most preferably from 4 mm to 2 mm.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

Primary/Secondary Fluid Distribution Layer

One optional component of the absorbent core according to the present invention, indicated as layer 40 in FIG. 1, is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers.

b Fluid Storage Layer

Positioned in fluid communication with, and typically underlying the primary or secondary distribution layers, is a fluid storage layer (42). The fluid storage layer can comprise any usual absorbent material or combinations thereof. It preferably comprises absorbent gelling materials usually referred to as "hydrogel", "superabsorbent", hydrocolloid" materials in combination with suitable carriers, which are indicated as particles (43) in FIG. 1.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise particles of a substantially water-insoluble, slightly cross-linked, partially neutralised, polymeric gelling material. This material forms a hydrogel upon contact with water Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate. These layers can be joined to each other for example by adhesive or melting a polymeric powder binder (e.g. PE powder), by mechanical interlocking, or by hydrogen bridge bends. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Nonhomogeneous distribution can also refer to laminates of carriers enclosing absorbent gelling materials partially or fully.

An alternative are foam like or actual foam structures as liquid storage. There are open cell foams which absorb liquid and through chemical or surface interaction retain the liquid also under pressure. Such foams may be formed with a skin, thus providing on their wearer facing surface a smooth appearance which makes the use of a topsheet optional. Typical foams in this context are e.g. those disclosed in PCT publications WO 93/03699, WO 93/04092, WO 93/04113.

c Optional Fibrous ("Dusting") Layer

An optional component for inclusion in the absorbent core according to the present invention is a fibrous layer adjacent to, and typically underlying the storage layer identified by reference numeral 44 in FIG. 1. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention, and preferably is provided close to or as part of the primary or secondary fluid distribution layer or the fluid storage layer, are odor control agents such as zeolites, carbon black, silicates, EDTA or other chelates. Such agents are preferably provided in particulate form or as part of particles and can be provided together with the absorbent gelling material mentioned supra.

Backsheet

The absorbent article according to the present invention also comprises a breathable backsheet. The backsheet primarily has to prevent the extrudes absorbed and contained in the absorbent structure from wetting articles that contact the absorbent product such as underpants, pants, pyjamas, undergarments, and shirts or jockets, thereby acting as a barrier to fluid transport. In addition however, the breathable backsheet of the present invention permits the transfer of both water vapour and air through it and thus allows the circulation of air into and water vapour out of the article. The backsheet typically extends across the whole of the absorbent structure and can extend into and form part or all of sideflaps, side wrapping elements or wings, often present in sanitary applications.

According to the present invention a dual or multiple layer breathable backsheet composite is preferred in the absorbent article. According to the present invention suitable breathable backsheets for use herein comprise at least a first air permeable layer with apertures. Preferred breathable multilayer backsheets for use herein are those having both a high vapour and high air exchange.

The first layer which is characterizing for the present invention is indicated as layer 50 in the drawings. It is positioned below the garment facing surface of the absorbent core and the wearer facing surface of the optional second layer which is indicated as layer 52 in FIG. 1. The first layer is oriented such that it retards or prevents liquid from passing from the absorbent core towards the outside while allowing free air flow through it.

According to the present invention the optional second layer (52) needs to provide at least water vapour permeability so as to support breathability of the article. It is desirable that it also supports air permeability in order to further improve the comfort benefit from the breathability of the article. In this context suitable water vapour and air permeable layers include two-dimensional micro- or macro-apertured films, which can also be micro-or macroscopically expanded films, formed apertured films and monolithic films, as well as nonwovens, or wovens.

Suitable 2 dimensional planar layers of the backsheet may be made of any material known in the art, but are preferably manufactured from commonly available polymeric materials. Suitable materials are for example Goretex (TM) or Sympatex (TM) type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures do not protrude out of the plane of the layer (in contrast to so called formed films). The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured preformed films have a directional liquid transport and are positioned such that they support the prevention of liquid loss (leakage) through the backsheet. Suitable macroscopically expanded films for use herein include films as described for example in U.S. Pat. Nos. 4,637,819 and 4,591,523.

Suitable monolithic films include Hytrel (TM), available from DuPont Corporation, USA, and other such materials as described in Index 93 Congress, Session 7A "Adding value to Nonwovens", J-C. Cardinal and Y. Trouilhet, DuPont de Nemours international S.A, Switzerland. Suitable nonwovens and/or wovens are any of those well known in the art. Non-wovens such as spunbonded, melt blown or carded which are thermobonded airlayed, drylayed or even wetlayed with or without binder or composites of such non-wovens in layered of mixed forms can be used. Particularly preferred non-wovens are multilayer non-wovens such as a composite of fine melt blown fibers with more coarse spunbonded fibers with the meltblown fibers forming the wearer facing surface of the non-woven layer, such as those disclosed in Whitehead, U.S. Pat. No. 4,578,069.

The first layer according to the present invention is preferably in direct contact with the absorbent core. It provides air and water vapour permeability by being apertured. Preferably this layer is made in accordance with the aforementioned U.S. Pat. No. 5,591,510 or PCT WO-97/03818, WO-97/03795. In particular, this layer comprises a polymeric film indicated in FIG. 1 as first layer (50), having capillaries (54). The capillaries extend away from the wearer facing surface of film (50) at an angle which is less then 90 degrees. In FIGS. 2 through 4 alternative embodiments of such capillaries are shown. Preferably the capillaries are evenly distributed across the entire surface of the layer, and are all identical. However, layers having only certain regions of the surface provided with apertures, for example only an area outside the region aligned with the central loading zone of the absorbent core, maybe provided with capillaries according to the present invention.

Methods for making such three-dimensional polymeric films with capillary apertures are identical or similar to those found in the apertured film topsheet references, the apertured formed film references and the micro-/macroscopically expended film references cited above. Typically a polymeric film such as a polyethylene (LDPE, LLDPE, MDPE, HDPE or laminates thereof) or polypropylene (or even a water vapour permeable film such as those disclosed for the optional second layer) is heated close to its melting point and exposed through a forming screen to a suction force which pulls those areas exposed to the force into the forming apertures which are shaped such that the film is formed into that shape and, when the suction force is high enough, the film breaks or raptures at its end thereby forming an aperture through the film.

Various forms, shapes, sizes and configurations of the capillaries are possible and have been discussed in the art. The apertures (53) form capillaries (54) which have side walls (56). The capillaries extend away from the wearer facing surface of the film (55) for a length which is at least such that it allows the aperture at the end of the capillaries to extend far enough away from the aperture at the opening of the capillaries that the capillaries can collapse completely when compressed to eliminate liquid transport in the collapsed state.

The capillaries have a first opening (57) in the plane of the garment facing surface of the film (55) and a second opening (58) which is the opening formed when the suction force (such as a vacuum) in the above mentioned process creates the aperture. Naturally the edge of the second opening (58) may be rugged or uneven, comprising loose elements extending from the edge of the opening as shown in FIG. 3 and 4. However, it is preferred that the opening be as smooth as possible so as not to create a liquid transport entanglement between the extending elements at the end of the second opening (58) of the capillary (54) with the absorbent core (44) in the absorbent article (in contrast this may be desirable for apertured film topsheets where such loose elements provide the function of sucker feet).

In one preferred embodiment according to the present invention as shown in FIG. 1 the capillaries extend "over" each other due to their angle and their length. This can be achieved when the center point of the second opening (as defined below) extends over or beyond of the center point of an adjacent capillary.

As shown in FIG. 4 the first opening has a center point (157) and the second opening also has a center point (158). These center points for non-circular openings are the area center points of the respective opening area. When connecting the center point (157) of the first opening (57) with the center point (158) of the second opening (58) a center axis (60) is defined. This center axis (60) forms an angle (59) with the plane of the film which is the same plane as the garment facing surface of the film (55). This angle should be preferably in the range between 85 and 20 degrees, more preferably between 65 degrees and 25 degrees, and most preferably between 55 and 30 degrees.

It is of course possible to allow the capillaries to take the shape of a funnel such that the second opening (58) is (substantially) smaller than the first opening (57) when considering the opening size in a plain perpendicular to the center axis (60). Such an embodiment is shown in FIG. 3 and FIG. 2. In FIG. 2 it is also shown that the wall (56) of the capillary may not end in the second opening (58) such that the opening forms a surface perpendicular to the center axis (60) but such that the wall on the portion of the capillary further apart from the wearer facing surface of the film (55) extends over the opening to aid the film in reducing the probability of liquid migrating through the capillaries from the absorbent core on the wearer facing side of the film (55) to the garment facing side of the film (and cause leakage).

Without wishing to be bound by theory it is believed that the capillaries according to the present invention in the first layer of the breathable backsheet allow air and water vapour permeability which is not hindered by them being slanted at an angle or by the shape as indicated above. At the same time the length slanting and shaping according to the present invention will enable the capillaries to close completely under pressure excerpted from the wearer facing side on them such that liquid transport through the capillaries towards the outside of the article becomes less likely when increasing the pressure while not completely loosing their (air and) water vapour permeability. Hence these three-dimensional formed film layers are highly preferable in the context of breathable absorbent articles and in particular so if an additional second outer layer is provided.

According to the present invention and as defined in the appended claims the first layer in the slanted capillary film backsheet does provide a certain liquid water transport resistance increase when comparing ambient pressure and a compression at a pressure at 6865 Pa. This increase is measured with a modified DIN 53886 test. At the same time the water vapour permeability can be measured also at ambient pressure and at the respective compression at a pressure of 6865 Pa. This water vapour permeability according to the present invention and as defined in the appended claims is reduced by less than 80%, preferably by less than 60%. Absorbent articles utilizing air and water vapour permeable backsheets according to this invention hence have the benefit of reducing liquid strike through problems under stress conditions i.e. when exposed to increased compression while maintaining the benefit of breathability under such stress conditions.

In the following the test for liquid water transport resistance and for water vapour permeability in their modified versions are defined in detail as employed in the present invention.

Liquid Water Transport Resistance Test

The liquid water transport resistance (hereafter WTR) test is utilized to quantify the barrier properties of a breathable backsheet material according to the present invention. The test uses DIN 53866 as method except where noted otherwise.

Basic Principle of the Method

The basic principle of the test is to evaluate the transport resistance of apertured materials to distilled water. An apertured layer should be sufficiently open to allow air permeability but, without the passage of large quantities of liquid. To ensure that this test is sufficiently representative to the situations under which different absorbent articles are actually used distilled water is used as a representative fluid.

Method Execution

To determine the transport resistance of an apertured film a standard water proofness tester such as Textest FX 3000 (manufactured by TexTest AG of Switzerland) water proofness tester, with a motor for continuous water pressure increase, is used. The water pressure is applied from below the sample so the wearer facing side of the sample has to be directed downwards towards the water.

In this test water pressure is measured at the moment of penetration through a sample. In order to exclude random failure the pressure is taken at the time when the first droplets penetrate at a first location and when water penetrates at a third location. Both pressure values are averaged forming a single measurement.

The modification of this test according to the present invention is to test the respective apertured film sample without compression and under a compressive pressure. The compressive pressure is applied by placing the sample between two plates which plates have matching apertures and can be fixed parallel to each other.

The apertures in the plates need to be provided such that they are large enough to present no liquid barrier but small enough to create a uniform compression to the apertured film. This can be achieved e.g. by use of aperture having a diameter of about 50% of the smallest diameter of the apertures in the test sample.

Figure 6:
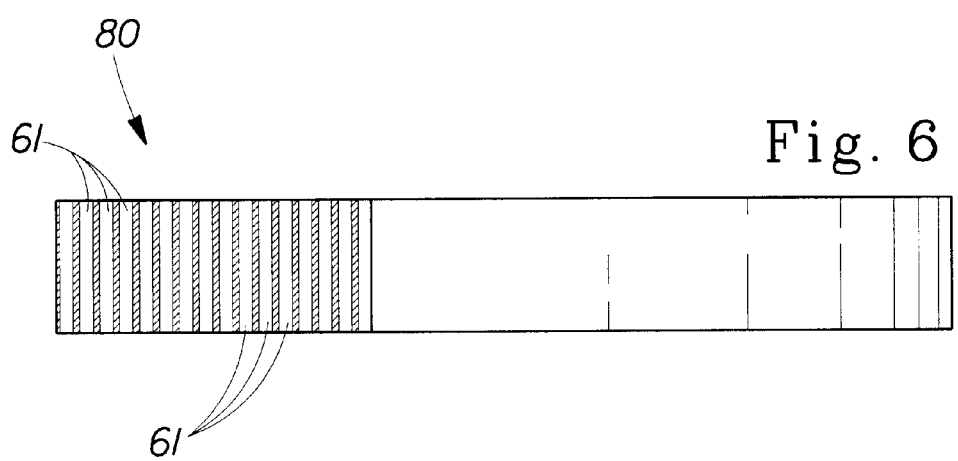

In FIGS. 5 and 6 a top plan view and a cross section of a sample plate (80) are shown. The total open area in a plate (80), is the sum of the areas of the apertures (61). The total open area should be as high as possible but at least 60% of the total area of the plate.

The compressed sample preparation is done by placing the sample between two plates and putting a weight on the plate which results in a compressive pressure of 6865 Pa when considering gravitational force of the weight divided by size of the plate including the apertures. This provide a pressure between the plates relative to each other in accordance with the compressed condition of the test. The plates are then mechanically maintained/fixed parallel to each other (i.e.at a spacing which maintains the compression) to allow removal of the weight.

In order for the test results to be comparable the uncompressed water transmission resistance is measured by use of a circumferencial spacing member between two plates which spacing member has to have at least the uncompressed thickness of the apertured film.

Interpretation of Test Results

The test result for both samples compressed and uncompressed is taken as the water pressure at the moment of water penetration through the sample. The water pressure is a linear proportional measurement of the water transport resistance, i.e. the higher the pressure measurement is the higher the water transport resistance of the sample is. For the comparison of the required increase of the water transport resistance according to the present invention a direct comparison of the water pressure at the moment of penetration according to this test method is used.

In accordance with the present invention the pressure at which liquid penetrates through the test material must be increased by at least 50% in the test using the compression relative to the test without compression. For samples which have no liquid penetrating through them already without compression the pressurized test is still necessary in order to see whether they maintain this excellent and most desirable result of no liquid transport through the test material. Obviously these materials cannot be considered according to the present invention since no improvement of liquid transport resistance can be achieved.

Water Vapor Permeability Test on Breathable Apertured Films

The Vapor permeability test is utilized to quantify the vapor transmission reduction of the apertured film under pressure.

Basic Principle of the Methods

The basic principle of the test is to quantify the extent of water vapour transmission of an absorbent article. The test method that is applied is a standard one, namely ASTM E 96-80, Procedure B—Water Method at 23° C. The test is performed in a stable temperature/humidity laboratory maintained at a temperature of 23° C. at 50% RH, all materials are conditioned at the laboratory conditions for a period of 24 hours. The vapor permeability value is determined as the weight loss in g divided by the open area of the sample holder in $m^2$ and quoted per day; i.e.:

Vapor Permeability=Weight Loss (g)/open area $(m^2)$/24 (hrs)

Modified Water Vapor Permeability Test

The modified test uses the same procedure as the basic water vapor permeability test including the respective test stand but placed on top of the side of the test material which is designated to be facing the absorbent core. In order to allow this the test also needs to be modified in that a standard absorbent structure is placed on that side of the film which is facing the absorbent core in an absorbent article. The standard absorbent structure in loaded with a sufficient quantity of water to ensure complete liquid water availability on the "inside" side of the test material. The cup of the ASTM test does then also not need to be filled with water any more.

The standard absorbent structure is composed of 4 layers (folded as a stack) of airlayed tissue of 63 g/$m^2$ basis weight {available from Walkisoft, USA under the supplier code Metmar(P50W.IPED)} having dimensions of 20 cm×6.5 cm. The test material which has the same dimensions is then placed on the bottom side of this structure without any additional adhesive attachment. Then a compressive load of 70 g/$cm^2$ (equivalent to 6865 Pa) is placed to the construction. This can be done with an apertured plate as used in the WTR test or similar. For comparison the open area has to be reconsidered in light of the reduced surface available for water vapor permeability when using an apertured plate. Alternatively to allow a direct comparison the plate can be used for the test with or without compressive pressure.

According to the present invention a test material which has successfully qualified under the water transport resistance test then has to maintain at least 80% of its water vapor permeability to fall within the present invention.

Air Permeability Test

The air permeability test is utilized to assess the ability of an absorbent structure to circulation/exchange air.

Basic Principle of the Methods

The basic principle of the test is to evaluate the resistance of an absorbent article to the passage of air. In this test, the volume (or amount) of air that flows through an article of given dimensions under standard conditions (of 23° C./50% RH) is measured. The instrument utilized for the test is: Air Permeabilimeter FX 3300 manufactured by TexTest AG Switzerland.

Samples should be allowed to equilibrate in the test environment for at least 4 hrs prior to commencement of the measurement. The article (having dimensions exceeding 5 cm$^2$ the dimensions of the measurement head) is placed on the device to measure the volume of air flow at a pressure drop of 1210 Pa that sucks air through the sample layer or structure. The device measures the volume of air flow and the pressure drop across the orifices that contains the sample and measurement head. Finally the device generates a value of air permeability in the units of liters/m$^2$/s.

Preferred articles according to the present invention have an air permeability in dry conditions without compressive pressure of not less than 1000 liter /m$^2$/s according to this test.

Absorbent Article Construction

According to the present invention the absorbent article can be used beneficially in the context of sanitary napkins, panty liners, incontinence articles, sweatpads, breast pads and diapers. However, sanitary napkins are particularly susceptible to the present invention. The disposable article may thus also have all those features and parts which are typical for products in the context of their intended use.

What is claimed is:

1. Breathable disposable absorbent article of layered construction, each layer or system of layers having a garment facing surface, which is oriented to face in the direction of a garment (21) during use of the article, and a wearer facing surface, which is oriented to face in the direction of the wearer (20) during use of the article, said article comprising at least an absorbent core (40, 42, 44);

a breathable backsheet (50, 52) located on said garment facing surface of said absorbent core (40, 42, 44), said backsheet (50, 52) comprising at least a first backsheet layer (50)

said first backsheet layers (50) being water vapor permeable, said first backsheet layer (50) comprising a resilient, three dimensional web, said web consists of a liquid impervious polymeric film (55) having apertures (53), said apertures (53) forming capillaries (54), said capillaries (54) having side walls (56) which extend away from said wearer facing surface of said film (55), said capillaries (54) having a first opening (57) in said garment facing surface of said film (55) and a second opening (58) at the end of said capillaries (54) spaced apart from said wearer facing surface of said film (55), said web has a liquid water transport resistance (WTR) in a direction from said second opening (58) towards said first opening (57) of said capillaries (54) measured by a modified DIN53886 test for WTR and said web has a water vapour permeability (WVP) in a direction from said second opening (58) towards said first opening (57) measured by a modified ASTM E 96-80 test for WVT of said capillaries (54), said article being characterized in that said WTR of said web increases at least 50% and said WVP reduces less than 80% when comparing WTR and WVP at ambient pressure with a compression of 6865 Pa above ambient pressure.

2. Breathable disposable absorbent article according to claim 1 characterized in that said capillaries (54) extend away from said wearer facing surface of said film (55) at an angle (59) of less than 90° measured from the plain of said film.

3. Breathable disposable article according to claim 1 characterized in that said capillaries (54) are all substantially identical, preferably said capillaries (54) are homogeneously distributed across said film (55) at a spacing which ensures the WVP reduces less than 80%, when comparing the values at ambient pressure 6865 Pa.

4. Breathable disposable article according to claim 1 characterized in that said WTR of said web increases at lest 65%, when comparing the values at ambient with a compression of 6865 Pa.

5. Breathable disposable article according to claim 1 characterized in that said first opening (57) of each of said capillaries (54) has a center point (157) and said second opening of each of said capillaries also has a center point (158) and a line connecting said center points defines a center axis (60) of each of said capillaries (54), said center axis (60) forming an angle (59) with the plane of said film (55), said angle being between 55° and 30°.

6. Breathable disposable article according to claim 1 claims characterized in that at least some of said capillaries form cones having liquid transport areas which are reducing in a direction areas towards the absorbent core (40, 42, 44) when comparing areas perpendicular to said center axis (60).

7. Breathable disposable article according to claim 1 characterized in that said capillaries (54) are curved towards said plane of said film.

* * * * *